United States Patent [19]

Papantonakos

[11] Patent Number: 4,769,006
[45] Date of Patent: Sep. 6, 1988

[54] HYDRODYNAMICALLY PROPELLED PACING CATHETER

[75] Inventor: Apostolos C. Papantonakos, Athens, Greece

[73] Assignee: KOS Medical Technologies, Ltd., Tampa, Fla.

[21] Appl. No.: 67,366

[22] Filed: Jun. 29, 1987

Related U.S. Application Data

[63] Continuation-in-part of Ser. No. 862,677, May 13, 1986, Pat. No. 4,717,381.

[51] Int. Cl.$^4$ .............................................. A61M 37/00
[52] U.S. Cl. ...................................... 604/95; 604/96; 128/672; 128/419 P; 128/786
[58] Field of Search ................... 604/95, 96; 128/672, 128/783–786, 419 P

[56]  References Cited

U.S. PATENT DOCUMENTS

| 1,115,908 | 11/1914 | Dees | 604/95 |
| 2,356,659 | 8/1944 | Aguiar | 604/95 |
| 2,393,728 | 1/1946 | Aguiar | 604/95 |
| 3,279,460 | 10/1966 | Sheldon | 604/95 |
| 3,937,225 | 2/1976 | Schramm | 128/419 P |
| 4,403,985 | 9/1983 | Boretos | 604/95 |
| 4,475,902 | 10/1984 | Schubert | 604/256 |
| 4,519,403 | 5/1985 | Dickhadt | 128/786 |
| 4,717,381 | 1/1988 | Papantonakos | 604/95 |

FOREIGN PATENT DOCUMENTS 2267800  11/1975  France ................................ 604/95

Primary Examiner—C. Fred Rosenbaum
Assistant Examiner—Gene B. Kartchner
Attorney, Agent, or Firm—Pettis & McDonald

[57]  ABSTRACT

A hydrodynamically propelled pacing catheter primarily intended for use in the placement of permanent pacemaker leads into the heart of a patient. The cephalic end of the catheter is constructed to define a plurality of nozzle orifices for the expulsion of a pressurized fluid so that the catheter will be propelled through the patient's vascular system into the heart. Dependent upon whether placement of the pacemaker lead is intended for the right atrium or the right ventricle, the catheter cephalic end will be curved or straight, respectively.

17 Claims, 6 Drawing Sheets

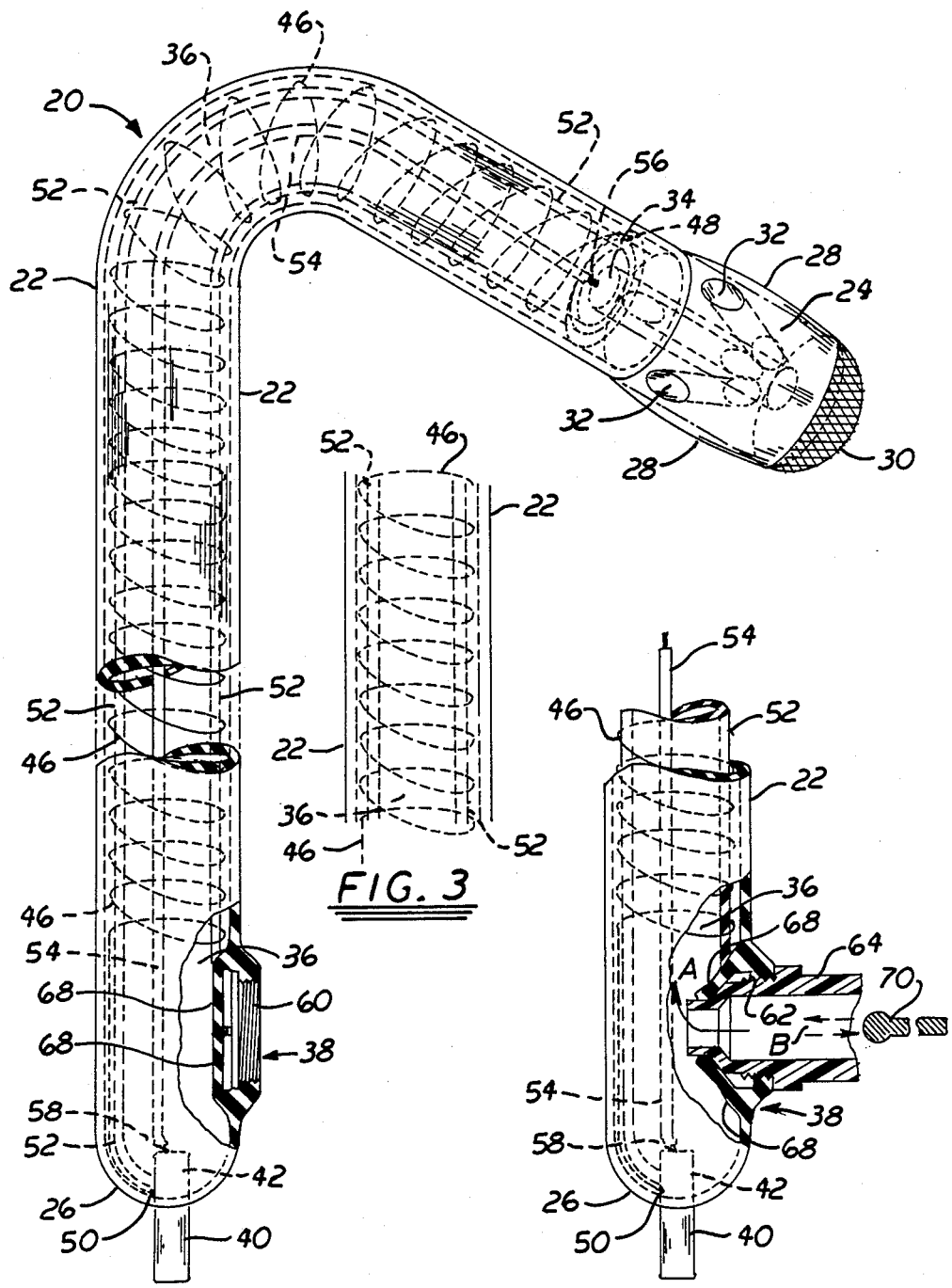

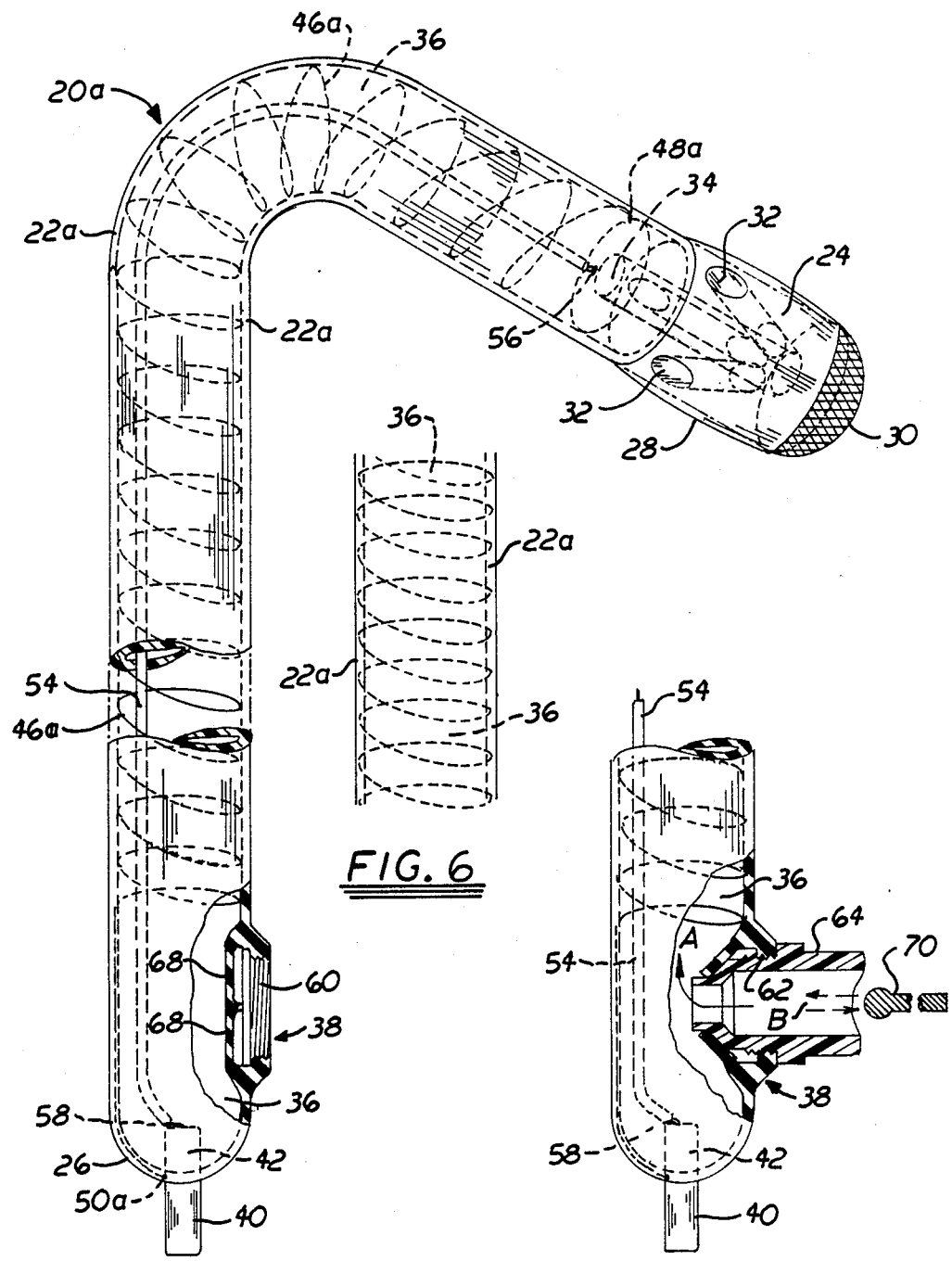

HYDRODYNAMICALLY PROPELLED PACING CATHETER

This application is a continuation-in-part of copending application Ser. No. 862,677, filed May 13, 1986, now U.S. Pat. No. 4,717,381.

BACKGROUND OF THE INVENTION

1. Field of the Invention

The present invention relates to a hydrodynamically propelled catheter for the placement of permanent pacemaker leads into the heart of a patient.

2. Description of the Prior Art

Modern cardiology would not have been nearly so successful if cardiac catheterization had not been realized, initially, for diagnostic and, subsequently, for therapeutic purposes. Cardiac catheterizations are conducted routinely today, with the results of such procedures normally being expressed in empirical measurements, and these measurements are used in both diagnosis and treatment.

A primary field of cardiac catheterization treatment is right atrium and right ventricle pacing by the insertion of permanent pacemaker leads into the right atrium and/or ventricle. According to today's relatively standard catheterization procedures, the cephalic end of the catheter is inserted through the subclavical vein or the cephalic vein into the patient's right atrium or right ventricle. Presuming that one wishes to position the pacemaker lead against the atrium appendage for right atrium pacing, proper placement and stabilization of the lead is extremely important in order to maintain positive electrical contact at all times. If one wishes to pass the lead from the right atrium into the right ventricle, perhaps the most delicate portion of the insertion procedure for right ventricle pacing is to pass the catheter through the tricuspid valve and stabilize it into the right ventricle. A primary purpose of the investigation and study resulting in the development of the hydrodynamically propelled catheter of this invention was to simplify entry into the right ventricle for the purpose of minimizing the operation time and, thus, to obtain the best stabilization in the right atrium and/or the right ventricle. As is set forth in greater detail below, as well as in my prior co-pending application identified above, it has been determined that the use of the hydrodynamically propelled catheter in accord with this invention efficiently and safely accomplishes those results, while at the same time significantly enhances proper placement of a right atrium pacemaker lead against the atrium appendage.

It is, of course, understood that numerous forms of cardiac catheters are well known in the prior art. Furthermore, a search of pertinent prior art literature has revealed the existence of devices constructed to utilize hydrodynamic forces during the catheterization procedure. Particularly pertinent ones of such prior art devices are disclosed in the "Description of the Prior Art" of my co-pending application identified above, and incorporated herein by reference.

Even though modern medical technology recognizes the necessity of a relatively swift, non-traumatic passage of the catheter through the tricuspid valve, as well as the necessity of precise and secure placement and stabilization of pacemaker leads against the atrium appendage and/or in the right ventricle, there appears to be no teaching in the prior patent literature of a catheter construction which will accomplish these results by the use of hydrodynamic forces. It is therefore clear that a great need in the art remains for a hydrodynamically propelled catheter construction specifically and uniquely designed for pacemaker lead insertion into the right atrium and/or right ventricle of a patient's heart.

SUMMARY OF THE INVENTION

Briefly stated, the catheter of this invention is in the nature of a heart catheter for inserting permanent pacemaker leads into the heart of a patient. Depending upon whether the lead is to be placed in the right atrium or the right ventricle, a normally curved or normally straight catheter, respectively, is selected pursuant to standard cardiac catheterization procedures.

Regardless of whether a curved or straight catheter is chosen, the cephalic end of the pacing catheter of this invention is constructed to include a plurality of rearwardly facing orifices, or ports. These ports are in fluid communication with a fluid lumen through which a pressurized fluid may be passed for expulsion through the ports. Because the ports are rearwardly oriented with respect to the cephalic end of the catheter, a propelling force, or thrust, will be imparted to the catheter upon passing the fluid therethrough. In accord with the disclosure of my co-pending application identified above and incorporated herein, valve means may be provided for regulating the flow of fluid through the fluid lumen and out of the ports.

Because the pacing catheter of this invention is intended for use in the placement of permanent pacing leads, a side lumen is formed through the catheter tube adjacent its rearward end in communicating relation to the fluid lumen, in order to connect a second catheter to the pacing catheter for the introduction of fluid through the fluid lumen and out the ports. As is more fully described hereinafter, the side lumen comprises means for self-sealing when no second catheter is connected thereto. It is also to be understood that the side lumen, with a second catheter operatively connected thereto, may also be utilized for the insertion of a standard guidewire of the type normally used to straighten a curved catheter during the insertion procedure.

Also as is more fully described hereinafter, the pacing catheter of this invention may be of either monopolar or bipolar construction. In the case of a monopolar pacing catheter, the tip of the cephalic end comprises a first pacing electrode. The rearward end of the pacing catheter is provided with a first electrical connector, and a first electrical conductor is operatively disposed in interconnecting relation between the first electrode and the first connector. The bipolar pacing catheter comprises a second electrode and corresponding second electrical connectors and conductors. With either a monopolar or bipolar catheter, the electrical connectors are dimensioned and configured for operative engagement with a source of pacing electricity from the pacemaker which is normally embedded subcutaneously on the patient's chest.

As will be set forth in greater detail hereinafter, the pacing catheter of this invention is characterized not only by the construction of its cephalic end to provide hydrodynamic propulsion, but also by its versatility of construction. As already indicated, the pacing catheter may be either monopolar or bipolar. Furthermore, a plurality of uniquely efficient constructions for the electrical conductors are disclosed, whereby the pacing catheter of this invention may be uniquely configured in response to its end use application, the materials selected for its various components, and the most desirable manufacturing techniques.

The invention accordingly comprises the features of construction, combinations of elements, and, arrangements of parts which will be exemplified in the constructions hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 1 is a plan view, partially in sections of a right atrium monopolar hydrodynamically propelled pacing catheter.

FIG. 2 is a fragmentary detailed view, partially in section, of the side lumen of the catheter shown in FIG. 1 with a secondary catheter connected thereto, and illustrating the insertion of a guidewire therethrough.

FIG. 3 is a fragmentary section of a segment of the pacing catheter of FIG. 1 illustrating means for insulating one embodiment of the first electrical conductor from the fluid lumen.

FIG. 4 is a view similar to that of FIG. 1 illustrating another embodiment of the right atrium monopolar hydrodynamically propelled pacing catheter of this invention.

FIG. 5 is a fragmentary detailed view, partially in section, of the side lumen of the catheter of FIG. 4 similar to the view of FIG. 2.

FIG. 6 is a fragmentary section of a segment of the pacing catheter of FIG. 4 similar to the view of FIG. 3.

Similar reference characters refer to similar parts throughout the several views of the drawings.

DETAILED DESCRIPTION

Figure 7:
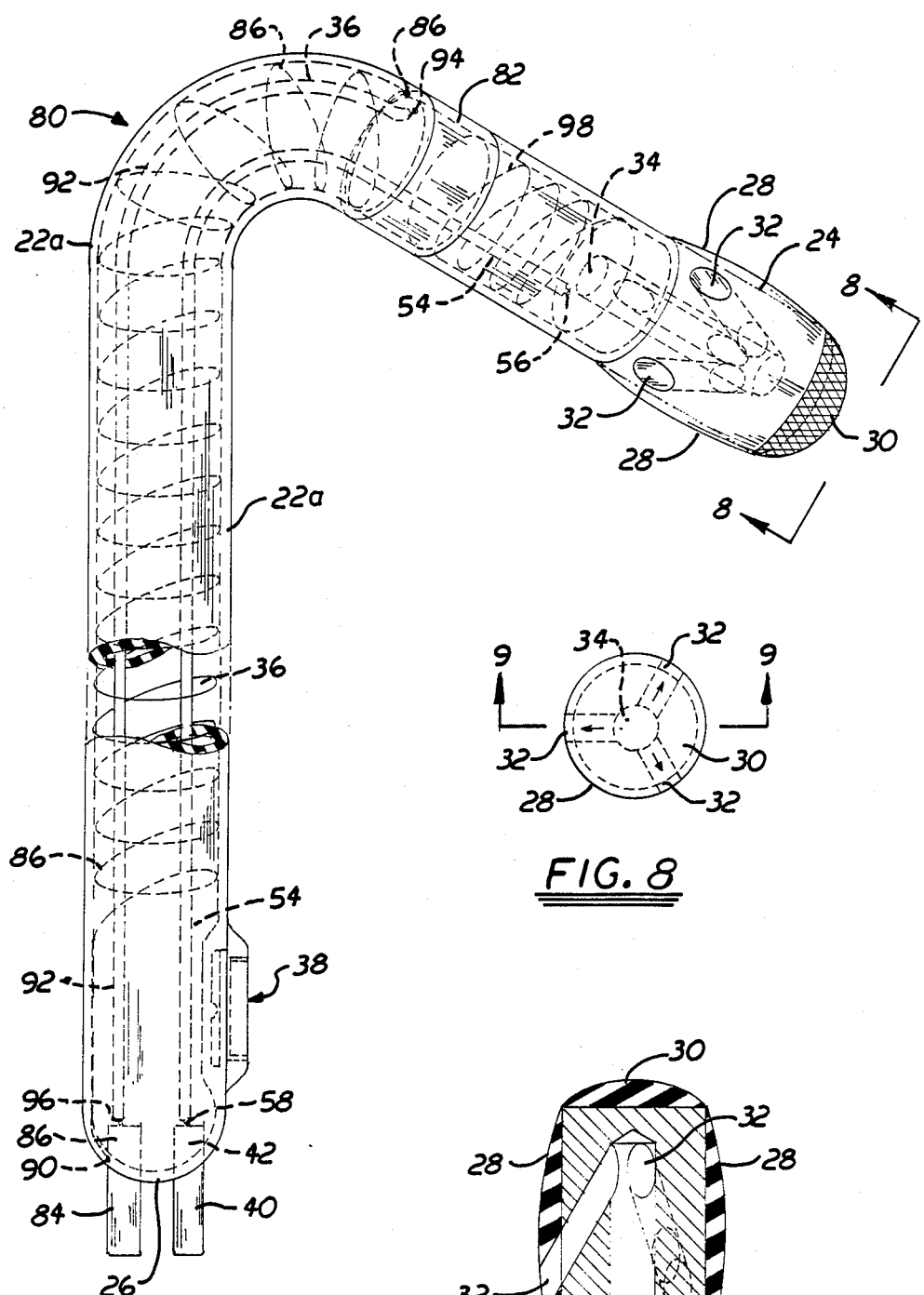
FIG. 7 is a plan view similar to that of FIG. 1 illustrating a right atrium bipolar hydrodynamically propelled pacing catheter.

While specific embodiments of a hydrodynamically propelled pacing catheter of this invention will be discussed below, certain general statements concerning catheter construction are relatively standard among all embodiments It is, of course, to be understood that these "standard" characteristics are presented for illustrative purposes only, in order to enable one skilled in the art to practice the invention described and claimed herein. The scope of the invention is not to be limited by these general characteristics or materials. It is also to be understood that the hydrodynamically propelled pacing catheter of this invention would be used in combination with other equipment and procedures normally utilized for heart catheterization for the purpose of inserting permanent pacemaker leads.

The main body of the catheter, or the catheter tube, may be formed of a variety of standard, substantially flexible materials. While the preferred embodiment of the catheter tube is formed from silicone rubber, other materials such as, for example, TEFLON, polyethylene, polyvinylchloride, or polyurethane may be employed. The preferred material for the conductive electrodes is iridium, though other materials may be utilized. Specific size considerations are not deemed critical to the scope of this invention, and the pacing catheter of this invention corresponds in size to other catheters currently in use. As already indicated above, the basic, normal configuration of the pacing catheter of this invention will either be curved, or substantially J-shaped, for placement of the lead against the right atrium appendage, or substantially straight for placement of the lead within the right ventricle. Utilization of the pacing catheter of this invention, and its insertion into the patient's heart, generally correspond to accepted medical procedures. However, by virtue of the construction of this pacing catheter to include hydrodynamic propulsion means, the user will experience enhanced mobility, greater speed and ease of insertion, particularly through the tricuspid valve, and improved placement and retention of the pacemaker lead against the wall of the patient's heart.

As a result of the theoretical studies and experimental work conducted with regard to the hydrodynamically propelled temporary catheter disclosed in my co-pending application identified above, it was realized that corresponding enhancement of permanent pacing lead catheters could be obtained by incorporating the means for providing hydrodynamic propulsion into those catheters. The enhanced mobility characteristics fully described in the detailed description of my co-pending application, identified above, are equally applicable in the instant construction for permanent pacing catheters. Accordingly, that disclosure and the corresponding calculations are incorporated herein by reference. It has also been determined that by virtue of providing means for hydrodynamic propulsion of pacing catheters, positive, permanent placement of the electrode against the heart is accomplished without the necessity of utilizing barbs, or hooks, adjacent the catheter tip. Therefore, should the need arise, the pacing catheter of this invention may be removed much more easily and safely than present permanent catheter leads.

Referring now to the view of FIG. 1, a first embodiment of a right atrium monopolar hydrodynamically propelled pacing catheter is generally indicated as 20. Pacing catheter 20 comprises an elongated flexible catheter tube 22 which may be formed, for example, from silicone rubber. Because the illustrated pacing catheter 20 is intended for use in the right atrium, it normally assumes a curved, or substantially J-shaped, configuration as shown in FIG. 1. Catheter tube 22 further comprises a cephalic end 24 and a rearward end 26. The cephalic end 24 is preferably formed from a conductive material such as iridium, and the major portion of the exterior surface of cephalic end 24 is covered with an insulating material 28 such as, for example, silicone rubber. The exposed tip of cephalic end 24 defines a first pacing electrode 30 of catheter 20.

As clearly seen in phantom in the view of FIG. 1, cephalic end 24 further comprises a plurality of rearwardly facing ports 32 which are substantially equally spaced around the perimeter of cephalic end 24. A central bore 34 is also provided axially through cephalic end 24, and central bore 34 is in fluid communication relation to each of the ports 32.

Figure 13:
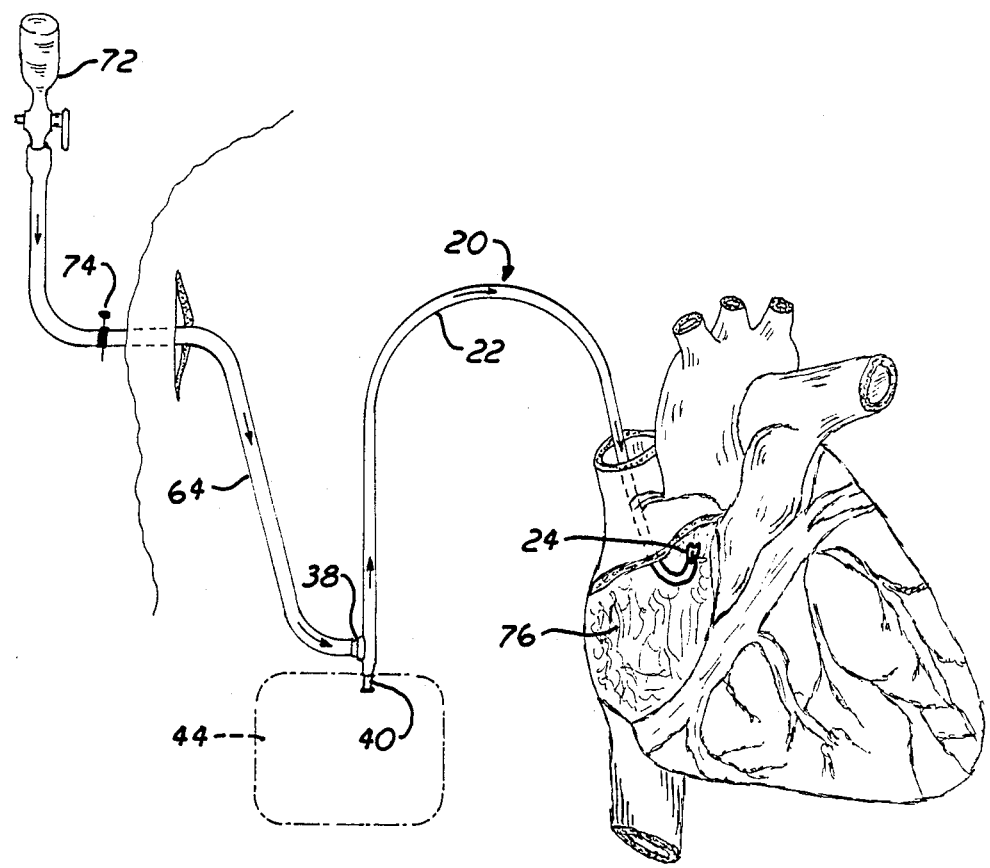
FIG. 13 is a schematic representation of a right atrium hydrodynamically propelled pacing catheter and pacemaker system during the implantation procedure.

The catheter tube 32 further comprises a fluid lumen 36 defined by a substantially open passageway which extends the length of catheter tube 22 from cephalic end 24 to rearward end 26. A distal end of fluid lumen 36 is in fluid communicating relation to ports 32 through central bore 34. A rearward end of fluid lumen 36 is defined by rearward end 26 of catheter tube 22 and is in communicating relation to a side lumen, generally indicated as 38, formed in catheter tube 22 substantially adjacent rearward end 26. Finally, a first electrical connector 40 is disposed through rearward end 26, and the interior segment 42 of connector 40 is insulated. As shown schematically in the view of FIG. 13, first electrical connector 40 is operatively connected to the pacemaker 44 which has been surgically inserted, subcutaneously, into the patient's chest.

The view of FIG. 1 illustrates two alternative means for conducting electrical energy from the pacemaker 44 to the first pacing electrode 30. Accordingly the first alternative, a first electrical conductor defined by a substantially helical wire 46 is disposed in interconnecting relation between the first pacing electrode 30 and the first electrical connector 40 as indicated at 48 and 50, respectively. Because helical wire 46 is conductive, it must be insulated from any fluid contained within the fluid lumen 36. While an insulating covering, or sheath, could be provided around helical wire 46, the view of FIG. 1 illustrates insulating means comprising a non-conductive flexible tube 52 disposed within and in spaced apart relation to the catheter tube 22. While any suitable material may be utilized for flexible tube 52, a preferred material is polyurethane. Details of this construction can be seen in the view of FIG. 3.

Alternatively, the means for conducting electricity may comprise a substantially linear first electrical conductor defined by wire 54. Respective ends of wire 54 are electrically connected to first pacing electrode 30 and first electrical connector 40 as indicated at 56 and 58, respectively. Preferably, wire 54 is covered with an insulating sheath (not indicated).

It is to be understood that if this alternative for the first electrical conductor conducting comprising wire 54 is selected, then the catheter 20 will not require the use of helical wire 46 or non-conductive flexible tube 52. In certain situations, however, depending upon the material chosen for catheter tube 22, one may find it desirable to retain either, or both, of the helical wire 46 and the non-conductive flexible tube 52. Obviously, if helical wire 46 were retained, the electrical connections indicated at 48 and 50 would be opened. In fact, in certain applications utilization of a non-conducting helical wire 46 in combination with conducting wire 54 would be necessary in order to retain the normal, curved configuration of catheter 20. If helical wire 46 is, in fact, conductive, then wire 54 would be eliminated.

Turning to the view of FIG. 2, structural details and utilization of side lumen 38 may be observed. Side lumen 38 comprises a threaded female connector 60 into which a similarly threaded male end 62 of a second catheter 64 may be inserted. As best seen in the view of FIG. 2, such insertion of second catheter 64 will cause distal end 66 of second catheter 64 to bias the sealing wings 68 outwardly, whereby material introduced through second catheter 64 may enter fluid lumen 36 as indicated by directional arrow A.

Still with regard to the view of FIG. 2, there is a fragmentary representation of a guide wire 70 of the type normally used for overcoming the normal curve of catheter 20 during its initial insertion. The insertion and the removal of guide wire 70 are indicated by directional arrows B. Additional utilization of side lumen 38 for the introduction of a fluid into catheter 20 so as to provide hydrodynamic propulsion is illustrated in the schematic view of FIG. 13. As shown therein, a source of fluid 72 is connected by a second catheter 64 to first catheter 20 at side lumen 38. So long as disconnect valve 74 is open and connected to source 72, fluid such as normal saline may flow through second catheter 64, into pacing catheter 20, and outwardly from cephalic end 24 of the pacing catheter 20, all as indicated by small directional arrows. Of course, cephalic end 24 would be straightened, as by a guide wire 70, during its initial insertion into right atrium 76. Alternatively, guide wire 70 could be inserted through connector 40. Once insertion had been accomplished, guide wire 70 would be removed and fluid exiting the ports of cephalic end 24 would ensure positive engagement of the first pacing electrode 30 with the atrium appendage.

Turning now to the view of FIG. 4, a second embodiment 20a of a right atrium monopolar hydrodynamically propelled pacing catheter may be seen. Insofar as the structural elements of second embodiment 20a correspond to structural elements of the first embodiment 20, identical reference numerals have been utilized. Accordingly, it can be seen that the significant difference between second embodiment 20a and first embodiment 20, both monopolar right atrium pacing catheters, is in the construction of the catheter tube 22a and the helical wire 46a. Referring to the sectional view of FIG. 6, the difference may be quite clearly observed. Helical wire 46a is insulated from fluid lumen 36 by forming catheter tube 22a to include the helical wire 46a embedded therein. In this embodiment one end 48a of helical 46a is operatively connected to the cephalic end 24, while the other end 50a of helical 46a is operatively connected to first electrical connector 40.

It is, of course, to be understood that the two means for conveying electricity from first connector 40 to first pacing electrode 30 are just as interchangeable in this embodiment 20a as previously described with respect to the first monopolar pacing catheter 20.

Turning now to the view of FIG. 7, one may see a first embodiment for a right atrium bipolar hydrodynamically propelled pacing catheter, generally indicated as 80. Inasmuch as substantial structural elements of this bipolar first embodiment 80 are identical to structural elements of the monopolar second embodiment 20a, identical reference numerals have been utilized to identify identical elements.

According to the construction shown for bipolar pacing catheter 80, in addition to the structural elements already described and identified with regard to the monopolar second embodiment 20a, bipolar catheter 80 further comprises a second pacing electrode 82 and a second electrical connector 84. The interior segment 86 of second electrical connector 84 would be provided with an insulating cover. The means for transmitting electricity from second connector 84 to second pacing electrode 82 may comprise a second helical wire 86 embedded within catheter tube 22a. One end of second helical wire 86 is operatively connected to the second pacing electrode 82 as indicated at 88, and the other end of second helical wire 86 is operatively connected to second electrical connector 84 as indicated at 90.

Alternatively, the electrical connection between second pacing electrode 82 and second connector 84 may be accomplished by a second wire 92 of substantially linear configuration. One end of wire 92 is operatively connected to second pacing electrode 82 as indicated at 94, and the opposite end is operatively connected to second connector 84 as indicated at 96.

It may also be seen that a spiral wire 98 may be provided within fluid lumen 36 intermediate the cephalic end 24 and the second pacing electrode 82.

Figure 8:
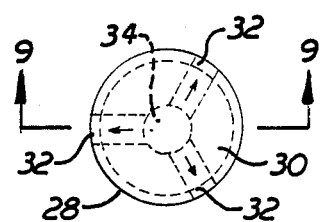
FIG. 8 is an end view of the bipolar pacing catheter taken along line 8—8 of FIG. 7.
Figure 9:
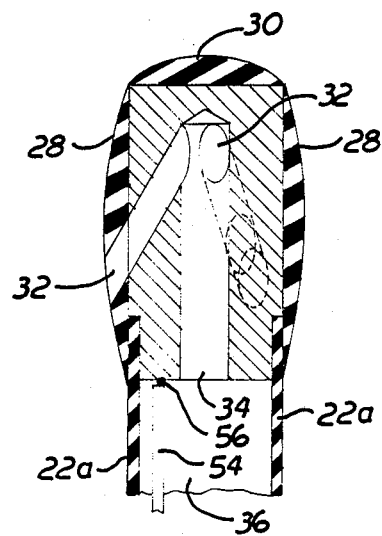
FIG. 9 is a sectional view taken along line 9—9 of FIG. 8.

As described with specific regard to first embodiment 20 and second embodiment 20a of the right atrium monopolar catheters, the scope of this invention is not limited by any particular selection of second helical wire 86 or second wire 92. In fact, as previously stated, second wire 92 may be selected for the purpose of conducting electrical energy, second helical wire 86 may be utilized in a non-conducting fashion to provide improved stability for this first embodiment 80 of the right atrium bipolar hydrodynamically propelled pacing catheter. Additional structural details of pacing catheter 80 are presented in the views of FIGS. 8 and 9.

Figure 10:
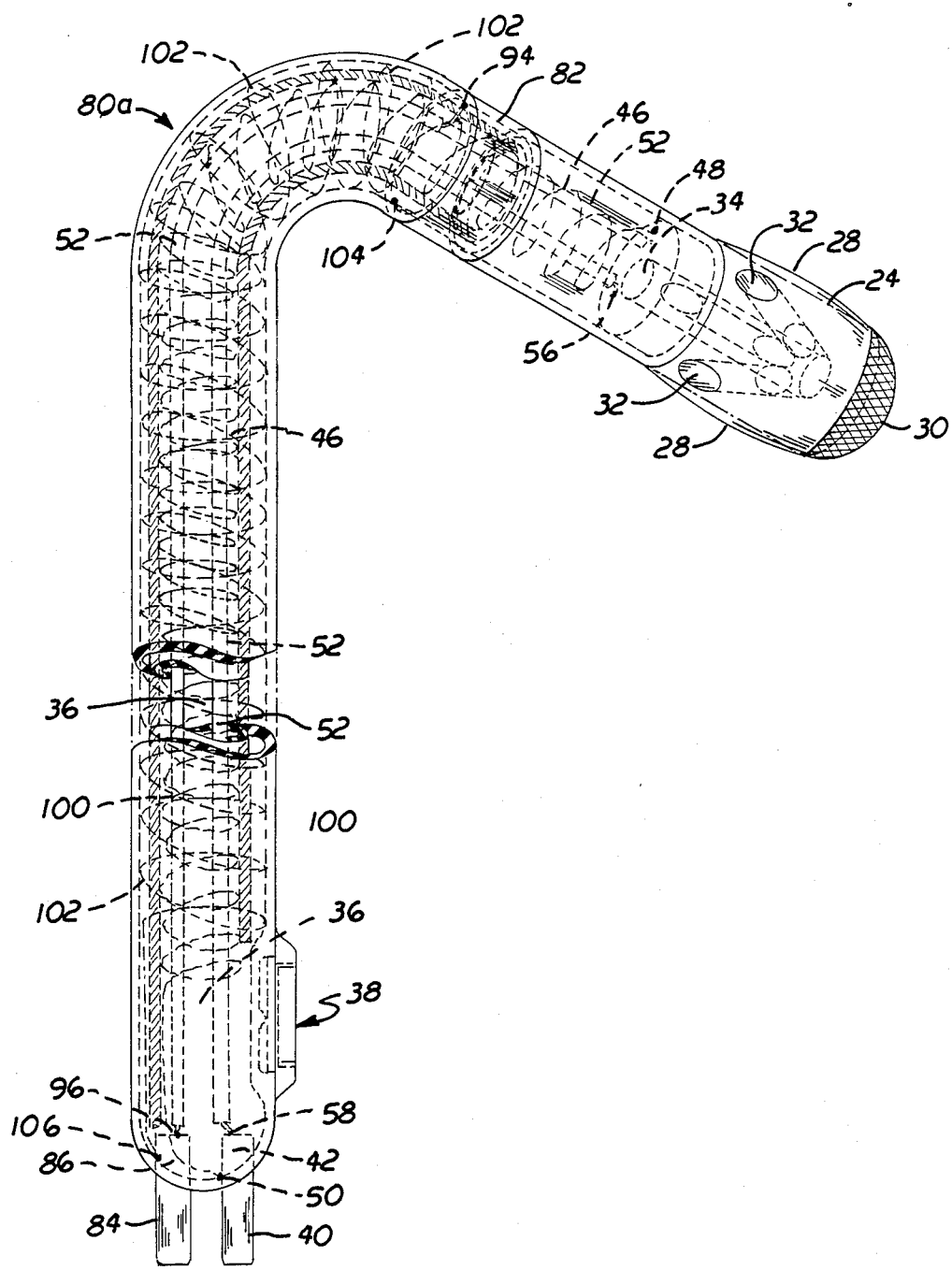
FIG. 10 is a plan view similar to that of FIG. 7 illustrating another embodiment for the right atrium bipolar hydrodynamically propelled pacing catheter.

In the view of FIG. 10, one may observe a second embodiment for a right atrium bipolar hydrodynamically propelled pacing catheter of this invention, generally indicated as 80a. By comparing the construction of this second bipolar catheter 80a with the construction of the first bipolar catheter 80 and the first monopolar catheter 20, one will recognize that the construction of FIG. 10 is essentially a bipolar embodiment of catheter 20. Accordingly, common structural elements have been identified by identical reference numerals. In this embodiment, a second non-conductive flexible tube 100 is provided, and a second helical wire 102 passes around second tube 100 with its ends making electrical contact at second pacing electrode 82 and second electrical connector 84 as indicated at 104 and 106, respectively. Accordingly, by virtue of the construction of this second embodiment 80a for the bipolar pacing catheter, at least four constructions can be observed:

1. Two helical wire conductors and no substantially linear wire conductors;
2. Two substantially linear wire conductors and no helical wire conductors;
3. A helical wire conductor to the first pacing electrode and a substantially linear wire conductor to the second pacing electrode; and
4. a substantially linear wire conductor to the first pacing electrode and a helical wire conductor to the second pacing electrode.

Figure 11:
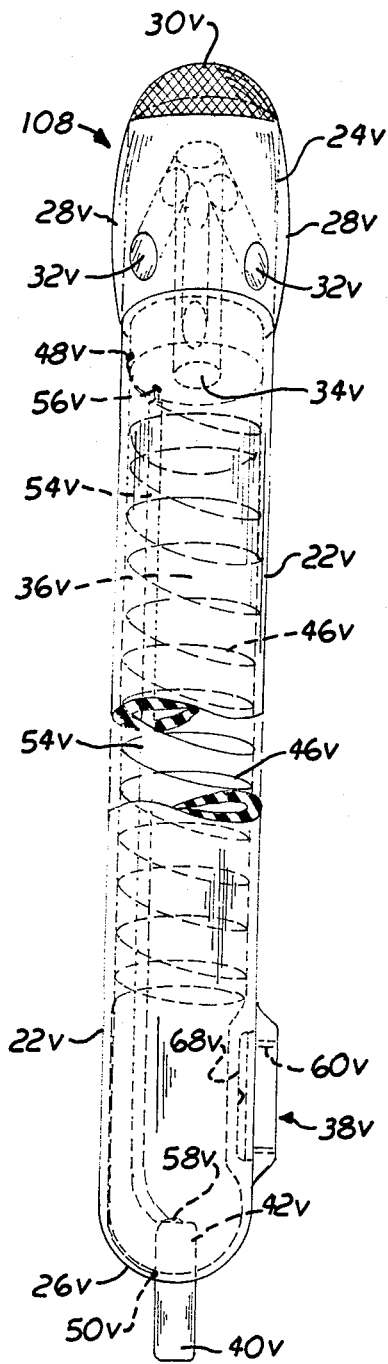
FIG. 11 is a plan view, partially in section, of a right ventricle monopolar hydrodynamically propelled pacing catheter.
Figure 12:
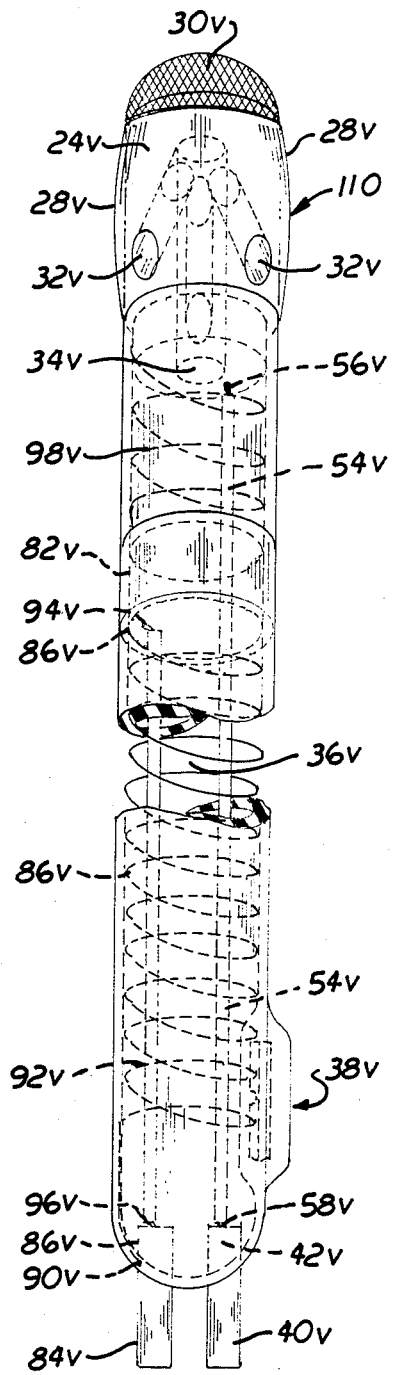
FIG. 12 is a plan view, partially in section, of a right ventricle bipolar hydrodynamically propelled pacing catheter.

The views of FIG. 11 and 12 illustrate right ventricle hydrodynamically propelled pacing catheters. In FIG. 11, there is generally indicated as 108 a right ventricle monopolar hydrodynamically propelled pacing catheter.

The structure for a right ventricle monopolar pacing catheter 108 as shown in the view of FIG. 11 is substantially identical to the construction for the right atrium monopolar hydrodynamically propelled pacing catheter 20a as shown in the view of FIG. 4. The only real difference between catheter 20a and catheter 108 is the straight, or non-curved, configuration of the right ventricle 108. Therefore, the structural elements of the monopolar right ventricle catheter 108 have been identified by reference numerals corresponding to those in FIG. 4 with the addition of a lower case letter "v." It is to be noted and understood that, alternatively, right ventricle monopolar pacing catheter 108 could be constructed in substantially identical fashion to that of the monopolar right atrium catheter 20, as shown in the view of FIG. 1.

The view of FIG. 12 illustrates a right ventricle bipolar hydrodynamically propelled pacing catheter, generally indicated as 110. Because the structure of bipolar right ventricle catheter 110 is substantially identical to the structure of bipolar right atrium catheter 80, similar reference numerals have been utilized in the view of FIG. 12 as in the view of FIG. 7 with the addition of the lower case letter "v" to each number. As above, however, it is to be understood that the right ventricle bipolar hydrodynamically propelled pacing catheter could be constructed in comparable fashion to second embodiment 80a of the right atrium bipolar catheter as shown in the view of FIG. 10.

Figure 14:
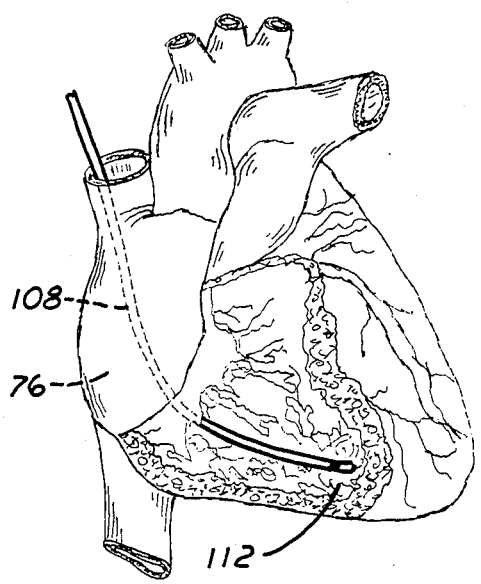
FIG. 14 represents a right ventricle hydrodynamically propelled pacing catheter in position in the patient's heart.

The view of FIG. 14 represents insertion of a right ventricle monopolar hydrodynamically propelled pacing catheter 108 into the right ventricle 112. It is when making this insertion through the tricuspid valve that the hydrodynamic propulsion efficacy is most evident, as fully set forth in my co-pending application identified above.

Figure 15:
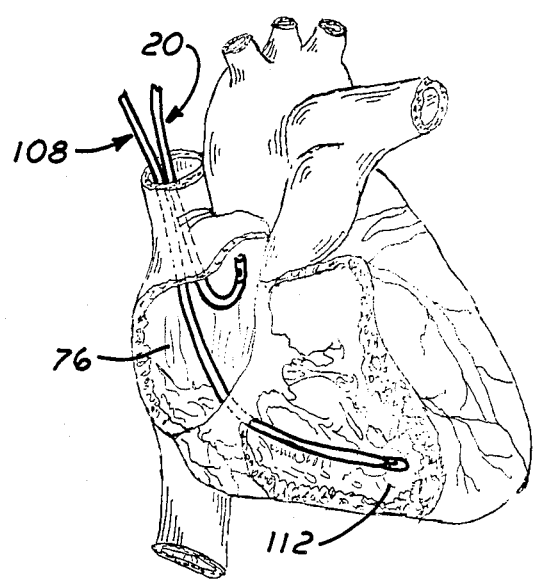
FIG. 15 depicts both a right atrium and a right ventricle hydrodynamically propelled pacing catheter operatively positioned in the patient's heart.

The final FIG. 15 illustrates operative placement of a monopolar right atrium catheter in the right atrium 76, and a monopolar right ventricle catheter 108 in the right ventricle 112.

Having thus set forth a number of constructions for both right atrium and right ventricle monopolar and bipolar hydrodynamically propelled pacing catheters, attention is invited to a brief description of normal implantation procedures. For right atrium lead implantation, one first fills the catheter with normal saline (plus heparine) solution. The guide wire is inserted to straighten the cephalic end for insertion, and the catheter is normally inserted through the subclavical vein. Once inserted into the right atrium, the guide wire is removed, and fluid flow is initiated to ensure the proper, positive placement of the pacing electrode adjacent the atrium appendage. Once the implantation has been completed and verified, the surgical incision is closed, retaining the normal saline solution in the catheter and permitting it to operate for about one or two weeks. Once proper implantation has been verified, radiopaque dye is inserted into the catheter to replace the normal saline solution in order to verify proper positioning and stabilization of the catheter. Then, utilizing fluoroscopic verification, the same volume of carbon dioxide is injected into the catheter to evacuate the radiopaque dye. The second catheter through which the normal saline solution, radiopaque dye and carbon dioxide were injected is then removed by extra-body manipulation (unscrewing), whereby the side lumen seals. Permanent implantation is complete.

Substantially identical procedures are utilized for safe, efficient insertion of a right ventricle lead. Of course, the use of a guide wire is not necessary for right ventricle catheterization, and perhaps most importantly, the hydrodynamic propulsion system is utilized to its full advantage in passing from the right atrium, through the tricuspid valve, and into the right ventricle.

It will thus be seen that the objects set forth above, among those made apparent from the preceding description, are efficiently attained, and since certain changes may be made in the above constructions without departing from the scope of the invention, it is intended that all matter contained in the above description or shown in the accompanying drawings, shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A hydrodynamically propelled pacing catheter of the type primarily used for insertion of permanent pacemaker leads into the hearts of patients, said pacing catheter comprising: an elongated flexible catheter tube for insertion through the patient's blood vessels into the heart, said catheter tube having a cephalic end and a rearward end; said cephalic end including a plurality of rearwardly facing ports substantially equally spaced around the perimeter thereof; said catheter tube further having a fluid lumen disposed longitudinally inside said tube, a distal end of said fluid lumen being in fluid-communicating relation to said ports and a rearward end of said fluid lumen being defined by said rearward end of said catheter tube; said catheter tube further having a side lumen formed therein substantially adjacent said rearward end in communicating relation to said fluid lumen whereby a second catheter may be connected to said pacing catheter for the introduction of a fluid through said fluid lumen and out said ports to impart a forward thrust to said cephalic end; said pacing catheter further comprising a first pacing electrode, said first pacing electrode defining the tip of said cephalic end, a first electrical connector disposed on said rearward end of said catheter tube, and a first electrical conductor operatively disposed in interconnecting relation between said first pacing electrode and said first electrical connector, said first electrical connector being dimensioned and configured to operatively engage a source of electricity whereby an electrical stimulus may be applied to the patient's heart.

2. A hydrodynamically propelled pacing catheter as in claim 1 wherein the axis of each of said ports defines an angle with the axis of said cephalic end of from about 5 degrees to about 30 degrees.

3. A hydrodynamically propelled pacing catheter as in claim 2 wherein said angle is about 30 degrees.

4. A hydrodynamically propelled pacing catheter as in claim 1 wherein said angle is about 15 degrees.

5. A hydrodynamically propelled pacing catheter as in claim 1 wherein said angle is about 5 degrees.

6. A hydrodynamically propelled pacing catheter as in claim 1 further comprising means for insulating said first electrical conductor from said fluid lumen.

7. A hydrodynamically propelled pacing catheter as in claim 6 wherein said first electrical conductor comprises a wire.

8. A hydrodynamically propelled pacing catheter as in claim 7 wherein said means for insulating comprises a non-conductive sheath around said wire.

9. A hydrodynamically propelled pacing catheter as in claim 8 wherein said wire defines a substantially helical path from said first electrical connector to said first pacing electrode.

10. A hydrodynamically propelled pacing catheter as in claim 7 wherein said means for insulating comprises said catheter tube and wherein said wire is embedded within said tube.

11. A hydrodynamically propelled pacing catheter as in claim 10 wherein said wire defines a substantially helical path from said first electrical connector to said first pacing electrode.

12. A hydrodynamically propelled pacing catheter as in claim 7 wherein said means for insulating comprises a non-conductive flexible tube disposed within and in spaced apart relation to said catheter tube.

13. A hydrodynamically propelled pacing catheter as in claim 12 wherein said wire defines a substantially helical path from said first electrical connector to said first pacing electrodes around the outer surface of said flexible tube.

14. A hydrodynamically propelled pacing catheter as in claim 1 wherein said side lumen comprises means for self-sealing said side lumen when no second catheter is connected thereto.

15. A hydrodynamically propelled pacing catheter as in claim 1 wherein said catheter tube cephalic end is normally curved with respect to the major length of said tube, whereby said pacing catheter is normally positioned in the right atrium of the patient's heart.

16. A hydrodynamically propelled pacing catheter as in claim 1 wherein said pacing catheter is normally substantially straight, whereby said pacing catheter is normally positioned in the right ventricle of the patient's heart.

17. A hydrodynamically propelled pacing catheter as in claim 1 further comprising a second pacing electrode operatively disposed on said catheter tube in spaced apart relation to said first pacing electrode, a second electrical connector disposed on said rearward end of said catheter tube, and a second electrical conductor operatively disposed in interconnecting relation between said second pacing electrode and said second electrical connector, said second electrical connector being dimensioned and configured to operatively engage the source of electricity.

* * * * *